United States Patent
Kehr et al.

(10) Patent No.: US 7,229,406 B2
(45) Date of Patent: Jun. 12, 2007

(54) DEVICE FOR POSITIONING AT LEAST ONE OPTICAL COMPONENT INSIDE AN ENDOSCOPIC SYSTEM

(75) Inventors: Ulrich Kehr, Leinfelden-Echterdingen (DE); Siegfried Hoefig, Mühlheim (DE)

(73) Assignee: Karl Storz GmbH & Co. KG (DE)

( * ) Notice: Subject to any disclaimer, the term of this patent is extended or adjusted under 35 U.S.C. 154(b) by 346 days.

(21) Appl. No.: 10/849,351

(22) Filed: May 19, 2004

(65) Prior Publication Data
US 2005/0004435 A1    Jan. 6, 2005

Related U.S. Application Data

(63) Continuation of application No. PCT/EP02/12705, filed on Nov. 13, 2002.

(30) Foreign Application Priority Data
Nov. 19, 2001    (DE) ............... 101 57 075

(51) Int. Cl.
*A61B 1/06*    (2006.01)
(52) U.S. Cl. .............. 600/172; 600/173; 600/176
(58) Field of Classification Search ............. 600/163, 600/167, 168, 172, 173, 181; 359/381, 813, 359/672–675; 396/93, 96, 73–75; 351/233–236
See application file for complete search history.

(56) References Cited

U.S. PATENT DOCUMENTS

| | | | |
|---|---|---|---|
| 2,987,960 A | 6/1961 | Sheldon | 88/72 |
| 3,416,856 A * | 12/1968 | Humphriss | 351/233 |
| 3,856,000 A | 12/1974 | Chikama | 128/6 |
| 4,704,520 A | 11/1987 | Kanno et al. | 250/205 |
| 4,862,199 A | 8/1989 | Centkowski et al. | 354/62 |
| 5,852,519 A * | 12/1998 | Do et al. | 359/822 |
| 5,971,918 A * | 10/1999 | Zanger | 600/160 |
| 5,978,161 A | 11/1999 | Lemke | 359/824 |
| 6,068,592 A * | 5/2000 | Davis | 600/132 |

FOREIGN PATENT DOCUMENTS

| | | |
|---|---|---|
| DE | 2 328 595 | 1/1974 |
| DE | 35 15 612 C2 | 7/1990 |
| DE | 197 13 276 A1 | 10/1998 |
| DE | 197 13 276 C2 | 6/1999 |
| DE | 199 03 437 C1 | 8/2000 |
| DE | 101 57 075 A1 | 11/2003 |

* cited by examiner

*Primary Examiner*—John P. Leubecker
*Assistant Examiner*—Victoria Chen
(74) *Attorney, Agent, or Firm*—St. Onge Steward Johnston & Reens LLC

(57) ABSTRACT

A device for positioning at least one optical component inside an endoscopic system has a housing through which an optical axis of the endoscopic system extends and in which the at least one optical component is arranged. The at least one optical component can be pivoted into the beam path and back out of the beam path about a pivot axis extending substantially parallel to a longitudinal axis of the housing, the at least one optical component being arranged on a support which is pivotable about the pivot axis. A smallest distance of an inside wall of the housing from the pivot axis is smaller than a greatest distance of the pivot axis to an outer edge of the at least one optical component.

22 Claims, 4 Drawing Sheets

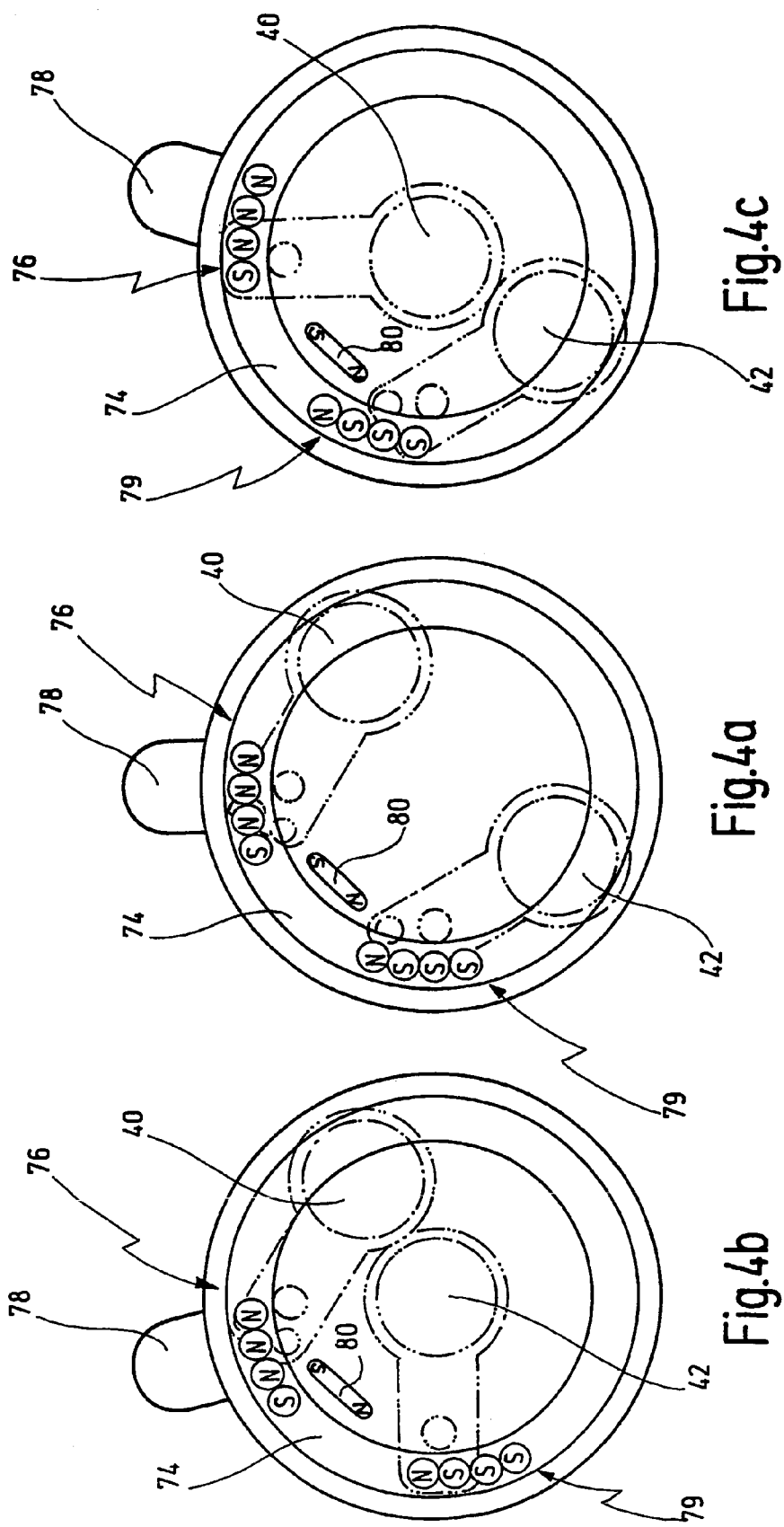

DEVICE FOR POSITIONING AT LEAST ONE OPTICAL COMPONENT INSIDE AN ENDOSCOPIC SYSTEM

CROSS REFERENCE TO OTHER APPLICATIONS

This application is a continuation of pending International Patent Application No. PCT/EP02/12705 filed Nov. 13, 2002 which designates the United States and claims priority of pending German Application No. 10157075.9 filed Nov. 19, 2001.

BACKGROUND OF THE INVENTION

The invention relates to a device for positioning at least one optical component inside an endoscopic system.

Within the meaning of the present invention, optical components are to be understood as, for example, lenses, filters, diaphragms, polarizers and the like, which can be used in an endoscope optic. Without restricting the generality of the invention, an optical component can also include a structural group made up of the aforementioned elements.

Within the meaning of the present invention, an endoscopic system can, for example, be an endoscope into which the device mentioned at the outset is integrated.

The beam path of the endoscopic system propagating along the optical axis can be the beam path of illuminating light propagating from proximal to distal and/or the beam path of observation light propagating from distal to proximal.

A particular application of the present invention is the use of a device mentioned at the outset in an endoscope for photodynamic diagnosis, for photodynamic therapy, or for diagnosis by fluorescence. In this particular application, the at least one optical component is normally a color filter to permit high-contrast observation of the tissue to be examined, free from the background radiation which is caused by the exciting light superposed on the observation light and which interferes with viewing. In addition, in this particular application of the device mentioned at the outset, conventional viewing of the tissue area with white light is also desired, so that such color filters not only need to be able to be brought easily into the beam path but also once again removed from it.

A device known from DE 197 13 276 A1 and used for positioning components inside endoscopic systems has, in one illustrative embodiment, a revolving wheel which rotates in the housing of the device about the longitudinal centre axis of the housing. The revolving wheel carries three optical components distributed in one plane, these optical components being able to be pivoted into and back out from the beam path of the endoscopic system about the longitudinal axis of the housing as the pivot axis. The longitudinal axis of the housing extends parallel to the optical axis but is a distance apart from it. This is disadvantageous, however, particularly in an endoscope, since the optical axis of an endoscope coincides with the longitudinal centre axis of the sometimes thin shaft of the endoscope. In the known device, this means that the housing of the device cannot be arranged concentric to or symmetrical with the longitudinal axis of the shaft, but rather extends beyond the shaft farther on one side than on the opposite side.

If one were to modify this known arrangement such that the housing of the device surrounds the optical axis of the endoscopic system concentrically or symmetrically, and assuming an unchanged diameter of the revolving wheel which cannot be made smaller because of the predetermined size of the optical components, the housing would have to be increased in diameter by about 1½ times, which would result in the disadvantage of a device taking up considerable space transversely with respect to the longitudinal axis.

Because the carrier is designed as a revolving wheel, the distance of a respective midpoint of the optical components to the pivot axis is relatively small, with the resulting disadvantage that the displacement of an adjustment member by the user of the device for pivoting the respective component into and back out from the beam path is very considerable. This disadvantage is heightened further by the fact that the distance of a driven element, provided on the revolving wheel, to the pivot axis is relatively large, since this distance cannot fall below a certain minimum amount, because otherwise the material bridge of the revolving wheel between two adjacent components is too narrow. Thus, the adjustment member has to travel a relatively great distance in order to switch the revolving wheel from one state to the next, which is an impediment to rapid and comfortable switching of the device.

In order to remedy this disadvantage, it has been proposed in DE 199 03 437 A1 to arrange the at least one optical component on an L-shaped carrier which is pivotable about a pivot axis extending transversely with respect to the longitudinal axis of the housing and thus transversely with respect to the optical axis of the endoscopic system. With this design of the device, it is possible to achieve, compared to the aforementioned known device, a housing with a smaller dimension transversely with respect to the longitudinal axis of the housing. In this known device, however, another disadvantage arises. For the at least one component pivotable into and out of the beam path, a gap corresponding to the thickness of the optical component is usually provided, extending in the direction of the longitudinal axis. In the axial direction, this gap is often bounded by other components of the endoscopic system, for example imaging lenses or diaphragms. In the direction of the optical axis, the gap for the component which is to be pivoted inward and outward should as far as possible be only slightly greater than the axial dimension of this component. However, because of the pivotability of the at least one component about a pivot axis extending transversely with respect to the optical axis and because of the associated range of pivoting, the at least one component requires a gap width in the axial direction which considerably exceeds the axial dimension of the component. The disadvantage of this known device thus lies in a structural restriction of the optical system as a result of the considerable range of pivoting of the component.

SUMMARY OF THE INVENTION

The object of the invention is therefore to develop a device of the type mentioned at the outset in such a way that the aforementioned disadvantages are avoided, in particular such that the housing of the device can be made as small as possible, according to the size of the at least one component, resulting in a small displacement travel of an actuating element for inward and outward pivoting of the at least one component.

According to the invention, a device for positioning at least one optical component inside-an endoscopic system is provided, comprising a housing having an inside wall and a longitudinal axis, an optical axis of the endoscopic system extending through said housing and defining a light beam path, at least one carrier carrying the at least one component, the carrier being pivotable about a pivot axis extending substantially parallel to the longitudinal axis of the housing so that the at least one component can be pivoted into the light beam path and back out of the light beam path about the pivot axis, the pivot axis being arranged such that a smallest distance of the inside wall of the housing from the pivot axis is smaller than a greatest distance of the pivot axis to an outer edge of the at least one component.

In the device according to the invention, in which the at least one optical component, in the same way as in the known device mentioned at the outset, is pivotable about a pivot axis extending parallel to the longitudinal axis of the housing, the revolving wheel is replaced by a carrier which avoids the disadvantages of the revolving wheel by virtue of the fact that a smallest distance of an inside wall of the housing from the pivot axis is smaller than a greatest distance of the pivot axis to an outer edge of the at least one component. In the device according to the invention, in contrast to the known revolving wheel, the pivot axis of the at least one component is accordingly located nearer to the inside wall of the housing, as a result of which any driven elements of an actuating device can be arranged near to the inside wall of the housing, resulting in an actuating device of simple design, and at the same time can be arranged near the pivot axis, resulting in a short actuation travel for inward and outward pivoting of the at least one component. Since the at least one component can be pivoted into and out of the beam path about a pivot axis extending parallel to the optical axis, the gap provided for this component can also be designed, in the direction of the longitudinal axis, with a narrowness corresponding exactly to the axial dimension or thickness of the optical component.

In a preferred embodiment, one dimension of the interior of the housing from the longitudinal axis to the inside wall of the housing in the pivot plane of the at least one component is about 1½ to 2 times as great as the greatest dimension of the at least one component in the pivot plane.

For this measure, it is sought to minimize the structural size of the housing of the device optimally as a function of the dimension of the at least one component. In the case of a housing with a round cross section and of a round component, the diameter of the interior of the housing corresponds for example to approximately three times the diameter of the optical component.

In another preferred embodiment, a distance of the outer edge of the at least one component from the pivot axis is in the range of between about a half to about three quarters of a dimension of the interior of the housing from the longitudinal axis to the inside wall of the housing, this distance preferably being about two thirds of said dimension.

This measure has the advantage that a very large pivoting movement of the at least one component can be achieved with a particularly short displacement travel of an adjustment member, and this permits switching of the device according to the invention between the pivoted-in and pivoted-out positions of the component. In the case of a housing with a round cross section, this means that the distance of the midpoint of the at least one component from the pivot axis lies in the range of approximately half the radius to approximately three quarters of the radius of the interior of the housing from the longitudinal axis, preferably approximately two thirds of the internal radius of the housing.

In a further preferred embodiment, at least two components are arranged in the housing, and each of these two components is assigned a separate carrier.

While it would also be conceivable to arrange two components on just one support, with their pivoting movements then necessarily being synchronized, the above measure has the advantage that, with a minimal size of the housing of the device, a total of three switching states can be obtained, namely two switching states in which alternately one of the two components or both is/are pivoted into the beam path, and a third switching state in which both components are pivoted out from the beam path.

In this connection, in a preferred embodiment, the carriers are arranged at axially about the same position relative to the longitudinal axis.

An advantage here is that the aforementioned gap, in which the at least one component comes to lie in the inwardly pivoted state, does not have to be made larger, and as a result of this the optical system of the endoscopic system does not suffer any structural limitations.

In a further preferred embodiment, the pivot axes of the carriers are offset by approximately 90° with respect to one another in the circumferential direction of the housing.

Particularly in combination with the aforementioned embodiment, this measure has the advantage that, with a minimal size of the housing of the device, the at least two components arranged at axially about the same position can be pivoted into and out of the beam path and the aforementioned total of three switching states are obtained.

In a further preferred embodiment, the carriers are arranged at axially different positions relative to the longitudinal axis.

This measure has the advantage that two optical components can also be pivoted simultaneously into the beam path, for example a filter and a polarizer, or a filter and a diaphragm, or two filters. This measure can be used not only as an alternative to, but also in conjunction with, the aforementioned embodiments, for example two components with their supports are arranged at axially the same position while a further pair of components is then arranged at an axial distance from the first pair. In this way, instead of a gap which is four times as great as an individual component, a gap which is twice as great may suffice for pivoting the four components into and out of the beam path.

In a further preferred embodiment, in order to pivot the at least one component, an actuating mechanism is provided which can be operated from outside the housing and which has at least one driver element cooperating with at least one driven element arranged on the carrier, in which case the distance of the at least one driven element from the pivot axis is small compared to the distance of a midpoint of the at least one component from the pivot axis.

This measure, which is made possible by the design of the device according to the invention, in contrast to the known revolving wheel, has the advantage that for the at least one component an actuating mechanism is provided which enables the user to execute a very short actuation displacement and thus affords a very rapid switching between the pivoted-in state and the pivoted-out state of the at least one component.

In this case, it is further preferred if the support is designed as a two-sided lever in relation to the pivot axis, the at least one carrier element being arranged on that side of the pivot axis directed away from the at least one component.

With regard to the construction of the actuating mechanism, this measure has the advantage that the driven element and the driver element can be arranged in direct proximity to the housing wall in order to obtain a force-fit connection or force transmission between the at least one driver element and the at least one driven element. A force-fit connection between the driver element and the driven element can be realized in the form of a mechanical connection (pin and hole), or, as in a further preferred embodiment, a magnetic force transmission in the form of a magnetic coupling can be provided.

In a further preferred embodiment, the actuating mechanism has an adjustment member on which at least one driver element is provided for each support, the driver elements cooperating with the driven elements in such a way that, when the adjustment member is moved from a starting position, in which both components are pivoted out from the beam path, to a first operating position, one component is pivoted into the beam path, and, when the adjustment member is moved from the starting position to a second operating position opposite to the first operating position, the other component is pivoted into the beam path.

An advantage here is that only one adjustment member is necessary to pivot the at least two optical components alternately into the beam path and out of it, or to pivot both components out of the beam path. In this way, the handling of the device according to the invention is improved still further, because it is possible to switch more quickly between the operating states of the device.

In a further preferred embodiment, in the first and second operating positions, the component respectively pivoted out is held securely in the pivoted-out position mainly by the interaction of the respective at least one driver element and the respective at least one driven element.

An advantage here is that components which might increase the susceptibility of the actuating mechanism to breakdown are not needed in order to hold the at least two components in the pivoted-in or pivoted-out position.

In a further preferred embodiment, the adjustment member can be locked in the starting position and the first and/or the second operating position.

An advantage here is that, after the inward or outward pivoting of the at least one component or preferably of the at least two components, the adjustment member can be released by the user without said adjustment member, and with it the at least one component, being shifted in an undesired way, for example due to gravity.

In a further preferred embodiment, the adjustment member is adjustable in the circumferential direction of the housing and has an operating lever.

An advantage here is that the device according to the invention can be operated and actuated in a way which is very straightforward and is not tiring for the operator.

In a further preferred embodiment, the at least one driver element and the at least one driven element are designed as magnetically acting elements and interact magnetically through the housing.

This measure has the advantage that the housing of the device can be designed such that it is hermetically sealed in its entirety, i.e. has no openings that have to be closed off by means of seals, and for this reason the device according to the invention is suitable for sterilization in an autoclave. Moreover, the device can in this way be integrated into the rest of the housing of an endoscopic system, for example of an endoscope, as a result of which the endoscopic system or endoscope as a whole can be designed with a housing which is hermetically sealed tight.

Further advantages and features of the invention will become evident from the following description and from the attached drawing.

It will be appreciated that the features mentioned above and those still to be discussed below can be used not only in the respectively cited combination but also in other combinations or in isolation, without departing from the scope of the present invention.

BRIEF DESCRIPTION OF THE DRAWINGS

An illustrative embodiment of the invention is shown in the drawings and is described in more detail below with reference to said drawings, in which:

FIGS. 4a) to 4c) show three diagrammatic representations of three operating states of a device used in the endoscopic system in FIG. 1 for the purpose of positioning optical components in the endoscopic system, FIGS. 4a) to c) corresponding to a section along the line IV—IV in FIG. 2.

DETAILED DESCRIPTION OF A PREFERRED EMBODIMENT

Figure 1:
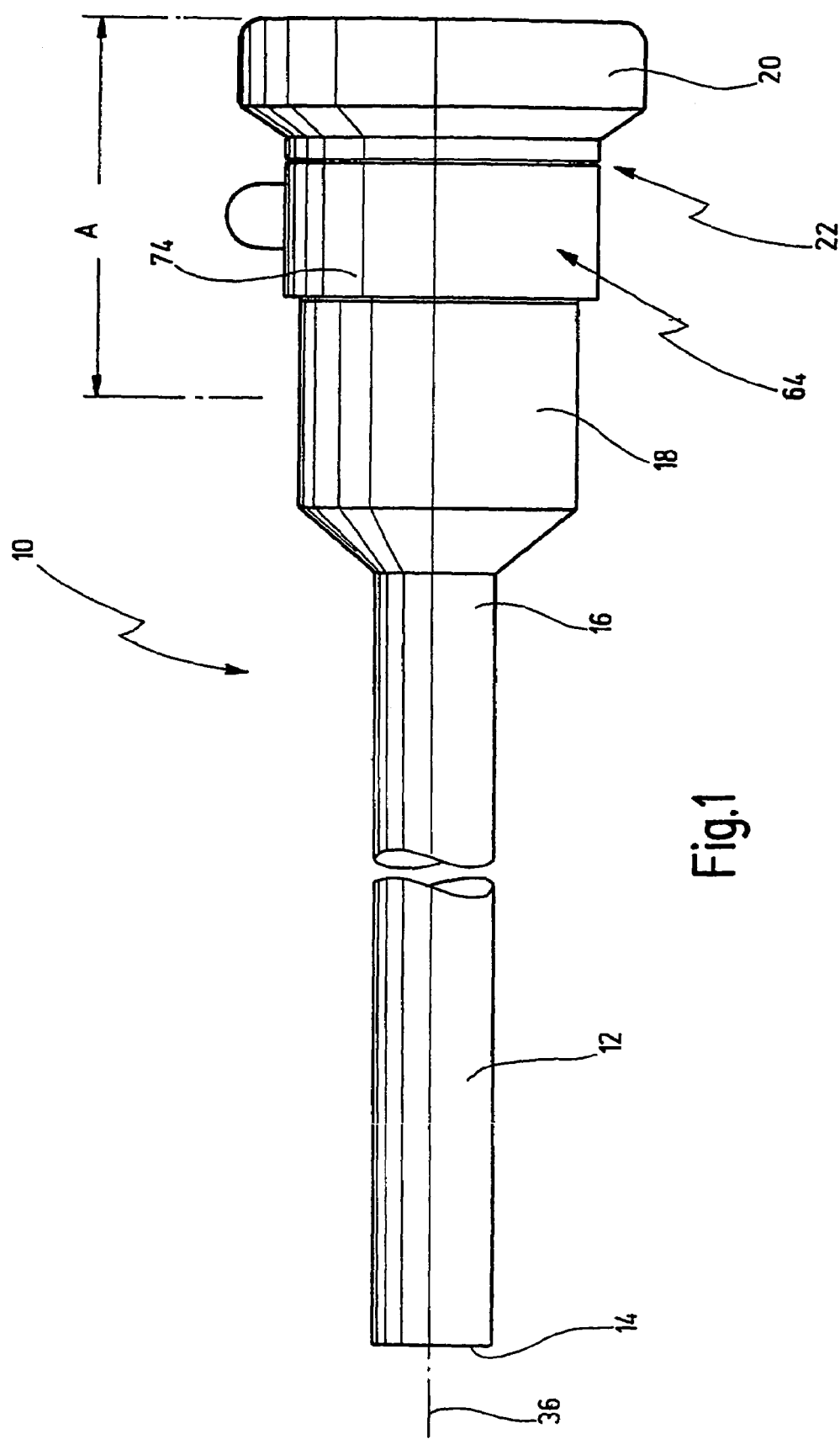
FIG. 1 shows an overall side view of an endoscopic system in the form of an endoscope.
Figure 2:
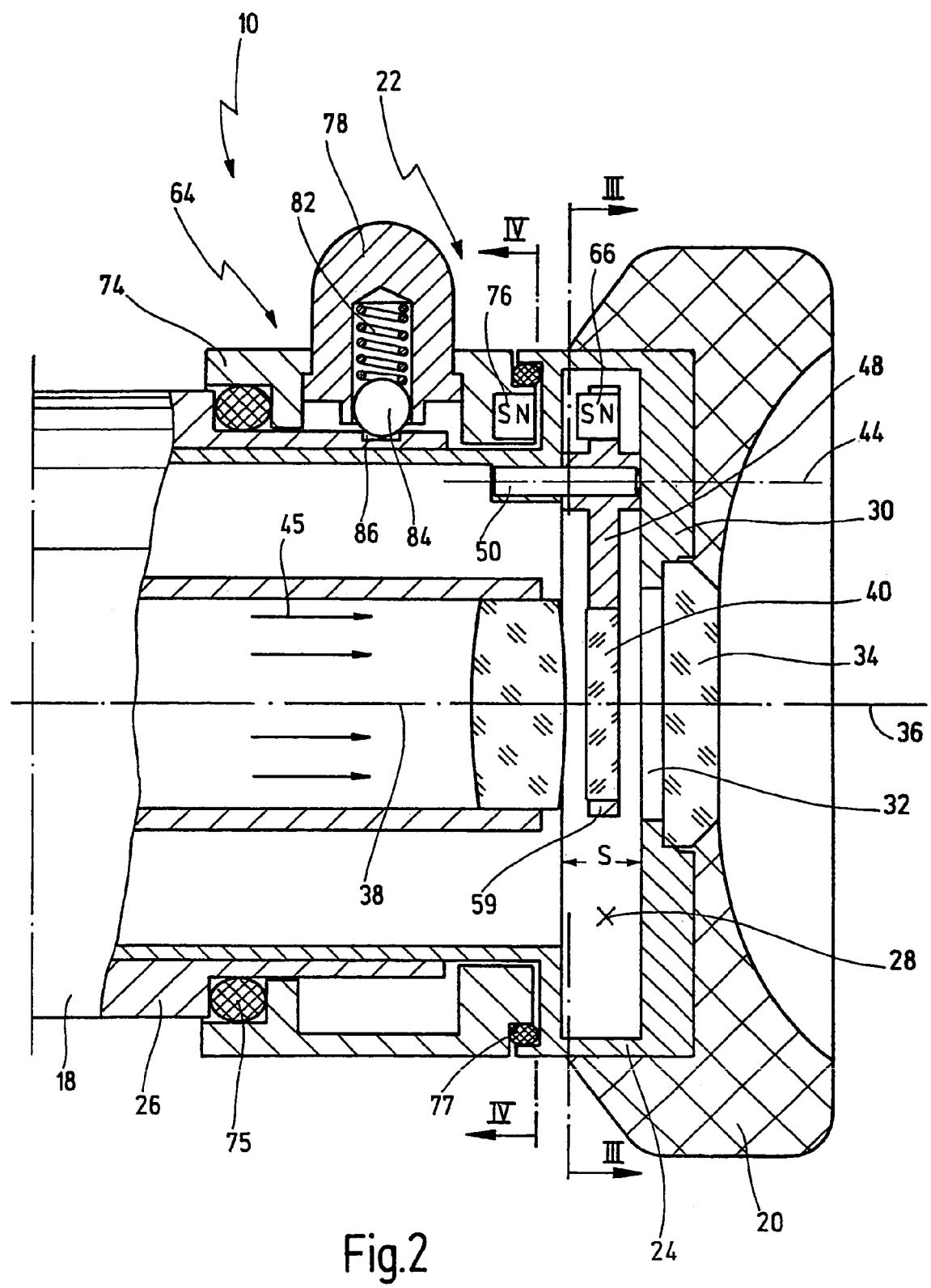
FIG. 2 shows the detail A in FIG. 1 in longitudinal section and on a larger scale than in FIG. 1, FIG. 2 being a section along the line II—II in FIG. 3.
Figure 3:
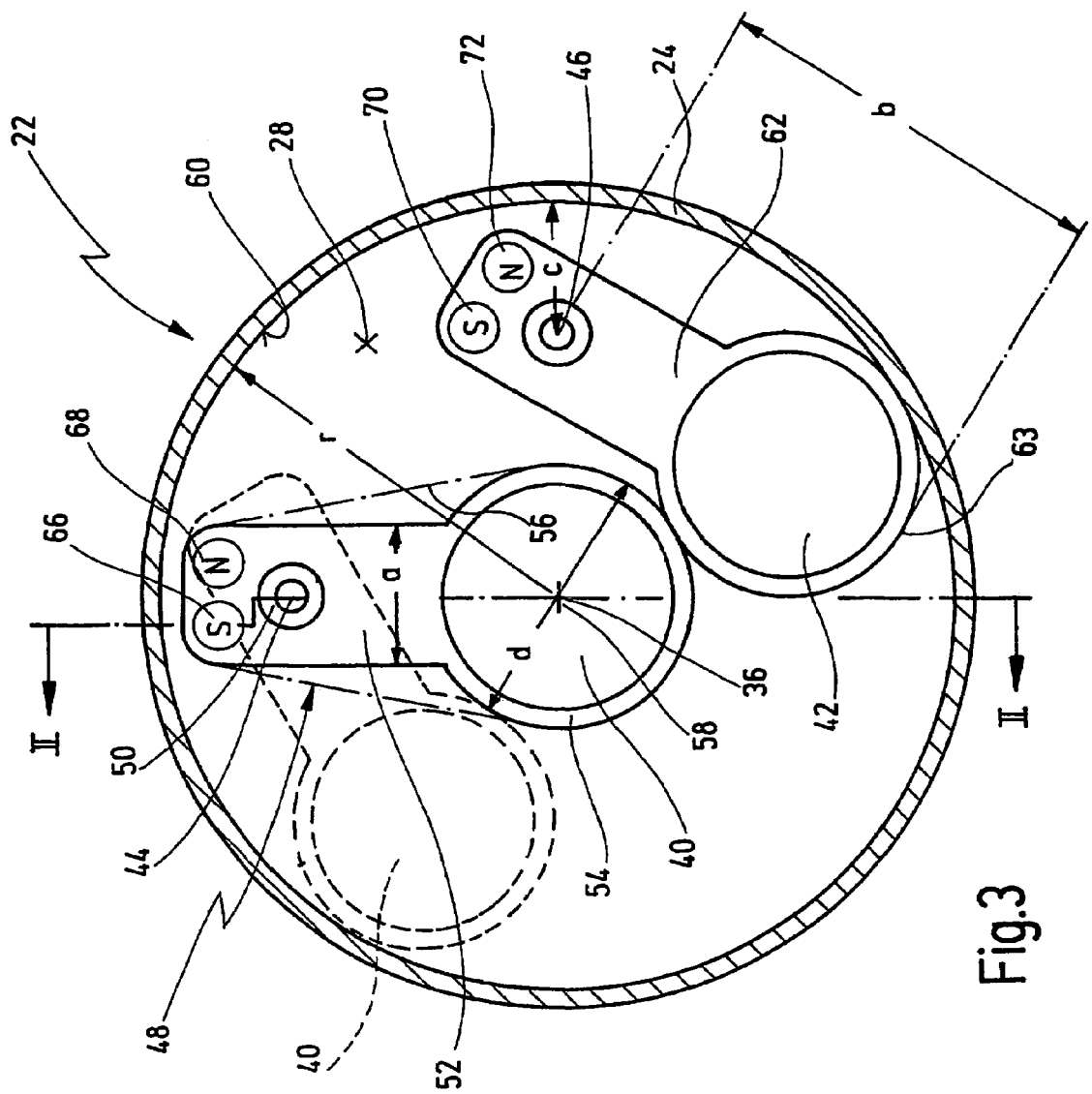
FIG. 3 shows a section along the line III—III in FIG. 2, the eyepiece cup in FIG. 2 having been omitted.

In FIG. 1, an endoscope designated by general reference number 10 is shown as an endoscopic system for photodynamic diagnosis or fluorescence-based diagnosis. Details of the endoscope 10 are shown in FIGS. 2 and 3, to which reference is likewise made below.

The depiction of the endoscope 10 in FIG. 1 is a diagrammatic one and is here intended to serve only for explanation.

The endoscope 10 has an elongate shaft 12 containing an optical imaging system (not shown) consisting of a number of lenses arranged in succession or of a coherent fiber-optic bundle and an incoherent fiber-optic bundle for the illuminating light. A distal end 14 of the shaft 12 forms the light entry port for observation light and the light exit port for illuminating light.

A proximal end 16 of the shaft 12 is adjoined by an optic head 18 or eyepiece which has an eyepiece cup 20 at its proximal end.

The endoscope 10 has a device, designated by general reference number 22, for positioning at least one optical component inside the endoscope 10, as will be described in more detail below with reference to FIGS. 2 and 3.

The device 22 has a housing 24. The housing 24 is in this case round in cross section and is connected securely to a housing 26 of the optic head 18, which housing 26 is likewise round in cross section. The housing 24 is also sealed off hermetically, i.e. an interior 28 of the housing 24 is sealed off hermetically from the outside environment. At its proximal portion 30 on which the eyepiece cup 20 is secured, the housing 24 has a light passage opening 32 which is closed off hermetically by a cover glass 34. "Hermetically" here means that the endoscope 10 can be sterilized in an autoclave without impurities or moisture being able to penetrate into the interior 28.

A longitudinal axis 36 of the housing 24, which axis here forms the longitudinal centre axis of the housing, and which also forms the longitudinal centre axis of the shaft 12, coincides with an optical axis of the endoscope optic of the endoscope 10.

At least one optical component is arranged in the housing 24, and, in the present illustrative embodiment, there are two optical components 40 and 42 arranged in the housing. The optical components 40 and 42 are, for example, two filters for different spectral regions.

The optical component 40 can be pivoted into the beam path (indicated by arrows 45 in FIG. 2) and back out again about a pivot axis 44 which extends substantially parallel, in this case exactly parallel, to the longitudinal axis 36 or optical axis 38. In FIGS. 2 and 3, the optical component 40 is shown in the state in which it has been pivoted into the beam path. By contrast, the optical component 42 has been pivoted out of the beam path. The optical component 42 can be pivoted into and out of the beam path about a pivot axis 46 which likewise extends parallel to the longitudinal axis 36 or optical axis 38.

The components 40 and 42 are arranged at axially the same position in relation to the longitudinal axis 36.

The pivot axis 46 is offset by approximately 90° in relation to the pivot axis 44 in the circumferential direction of the housing 24.

The component 40 is arranged on or fastened to a carrier 48 which is mounted so as to be pivoted about the pivot axis 44 by means of a pin 50 on the housing 24 of the device 22.

The carrier 48 has a first portion 52 and a second portion 54. The second portion 54 serves as a mount for the optical component 40 and is regarded in the present description as belonging to the optical component 40. However, it is also possible to secure the component on the portion 52 without the portion 54, so that the carrier 48 is understood as only the portion 52.

The carrier 48 on the whole is of elongate design and has, in the direction of the longitudinal axis 36, i.e. in the axial direction, a thickness which corresponds to approximately the thickness of the optical component 40. The carrier 48 extends substantially straight transversely with respect to the longitudinal axis 36.

In the pivot plane of the optical component 40 (drawing plane in FIG. 3), the carrier 48 has a greatest dimension a which is less than or equal to a greatest dimension d of the component 40 in the pivot plane. The greatest dimension d, i.e. in the present case with a circular component 40 the diameter of said component 40, is understood in the present case to also include the additional dimension of the second portion 54 of the carrier 48 which surrounds the component 40. The dimension a of the carrier 48 can therefore be also as great as the diameter of the component 40 inclusive of the second portion 54. This dimension is designated by d in FIG. 3. While the carrier 48 in the illustrative embodiment shown has substantially the shape of a rectangle, the carrier can also for example widen to the greatest diameter of the second portion 54, as is indicated by a dot-and-dash line 56. For the purposes of the invention, it is sufficient if, on that side which approaches the housing 24 when the component 40 is pivoted out from the beam path, the carrier 48 does not protrude beyond, or protrudes only marginally beyond, the optical component 40, so that the carrier 48 does not come to lie against the housing 24 before the component 40 has been pivoted completely out from the beam path.

A distance of, on the one hand, a midpoint 58 of the component 40 which coincides with the longitudinal axis 36 or optical axis 38 in the state when pivoted into the beam path and, on the other hand, an outer edge 59 from the pivot axis 44 is greater than half the dimension r of the interior 28 of the housing 24 from the longitudinal axis 36 to an inside wall 60 of the housing 24 in the pivot plane of the component 40. In the illustrative embodiment shown, in which the housing 24 is round in cross section, this means that the distance of the midpoint 58 of the component 40 from the pivot axis 44 in the pivot plane of the component 40 is greater than half the radius of the interior 28 of the housing 24.

The distance of the midpoint 58 of the component 40 from the pivot axis 44 lies preferably in the range of between about half the dimension r, i.e. half the radius of the interior 28 of the housing 24, to about three quarters of the dimension r of the interior 28 of the housing 24 from the longitudinal axis 36 to the inside wall 60 of the housing 24. In the illustrative embodiment shown, the distance of the midpoint 58 of the component 40 from the pivot axis 44 is approximately two thirds of the dimension r.

The dimension r of the interior 28 of the housing 24 from the longitudinal axis 36 to the inside wall 60 of the housing 24 in the pivot plane of the component 40 is approximately 1.5 to 2 times as great as the dimension d, i.e. the diameter d of the component 40 (in the illustrative embodiment shown, inclusive of the dimension of the second portion 54 of the carrier 48). This choice of the dimension r of the interior 28 of the housing 24 is thus sufficient to ensure that the component 40 can be pivoted completely out from the beam path, as is indicated in FIG. 3 by broken lines of the component 40. Moreover, this choice of the dimension r of the interior 28 of the housing 24 makes it possible to arrange the second component 42 at axially the same position as the optical component 40 in the housing 24, and also to allow this component 42 to be pivoted completely out from the beam path, with at the same time a minimum size of the housing.

The component 42 is arranged on a separate carrier 62 which, in the illustrative embodiment shown, is of identical design to the carrier 48 and, for this reason, does not have to be described in any detail here. Like the components 40 and 42, the carrier 62 lies at axially the same position as the carrier 48 in relation to the longitudinal axis 36, only the pivot axis 46 of the carrier 62 is arranged offset by approximately 90° from the pivot axis 44 of the carrier 48 in the circumferential direction of the housing 24.

As is shown for the component 42 with the carrier 62 in FIG. 3, while the same applies to the component 40 and the carrier 48, a smallest distance c of the pivot axis 46 from the inside wall 60 of the housing 24 is smaller than a greatest distance b of the pivot axis 46 to an in this case circumferential outer edge 63 of the component 42.

On account of the arrangement of the components 40 and 42, one of the two components 40 and 42 can in each case be alternately pivoted into the beam path, as is described in more detail below. However, it is also conceivable to arrange the components 40 and 42 at axially different positions, so that both components can then be pivoted simultaneously into the beam path, and in this case to provide more than two components.

As is shown in FIG. 2, a gap s in the direction of the longitudinal axis 36, which gap is provided for positioning the components 40 and 42 into the beam path, can be chosen so small that the gap s corresponds substantially to the axial dimension or thickness of the components 40 and 42. Thus, the device 22 is of very small construction not only transversely with respect to the longitudinal axis 36, but also in the direction of the longitudinal axis 36, i.e. axially.

Referring to FIGS. 1 to 4, an actuating mechanism 64 for pivoting the components 40 and 42 into and out of the beam path of the endoscope 10 is described in more detail below.

Arranged on the carrier 48 there is at least one driven element, and in the illustrative embodiment shown two driven elements 66 and 68, in the form of magnetically acting elements, for example small magnets which have opposite polarities. The letter S designates the magnetic south-pole and the letter N the magnetic north pole.

The distance of each driven element 66 and 68 from the pivot axis 44 is small compared to the distance of the midpoint 58 of the component 40 from the pivot axis 44. The carrier 48 is thus designed as a two-sided lever, in this case a straight lever, whose one lever arm is formed by the length between the driven elements 66, 68 and the pivot axis 44, and whose other lever arm is formed by the length between the pivot axis 44 and the midpoint 58 of the component 40. In the illustrative embodiment shown, the ratio of the lever arm lengths is approximately 1:4.

Arranged on the carrier 62 there are corresponding driven elements 70 and 72 which are positioned, in relation to the pivot axis 46, in the same way as the driven elements 66 and 68 in relation to the pivot axis 44.

The driven elements 66, 68 are arranged on that side of the pivot axis 44 directed away from the component 40, in the same way as the driven elements 70 and 72 are arranged on the carrier 62 on that side of the pivot axis 46 lying opposite the component 42 on switching.

The actuating mechanism 64 has an adjustment member 74 in the form of an adjustment ring which surrounds the housing 24 and which is inhibited by O-rings 75 and 77 in order to generate a displacement resistance which favors maneuvering.

A plurality of driver elements 76 and 79 are arranged on the adjustment member 74. Four driver elements 79 are assigned to the driven elements 66 and 68 of the carrier 48, while four driver elements 79 are assigned to the driven elements 70 and 72 of the carrier 62. The driver elements 76 and 79 are connected firmly to the adjustment member 74. The adjustment member 74 can be moved in the circumferential direction of the housing 24 in both directions of rotation about the longitudinal axis 36.

The driver elements 76 and 79 are likewise designed as magnetically acting elements, for example small magnets, and interact magnetically with the driven elements 66, 68 and 70, 72, respectively, through the housing 24.

The polarities or poles of the driver elements 76 and 79 are again designated by S and N.

For moving it in the circumferential direction of the housing 24, the adjustment member 74 has an operating lever 78, which can be actuated using the thumb for example.

As is shown in FIGS. 4a) to 4c), the actuating mechanism 64 permits three operating positions of the device 22.

FIG. 4a) shows a starting position in which both components 40 and 42 are pivoted out from the beam path. In this starting position, the components 40 and 42 are held in the pivoted-out position solely by the magnetic interaction between the driver elements 76 and 79 and the driven elements 66, 68 and 70, 72. For further securing of the position, a positionally fixed additional magnet 80 is optionally provided in the housing.

If, starting from FIG. 4a), the adjustment member 74 is now moved counterclockwise (FIG. 4b), the component 42 is pivoted into the beam path by the magnetic driver effect between the driver elements 79 and the driven elements 70 and 72, while the component 40 is held in the pivoted-out position by means of the magnetic interaction between the driven elements 66 and 68 and the driver elements 76 assigned to them. As will be apparent from a comparison of FIGS. 4a) and 4b), the path traveled by the adjustment member 74 in order to switch or pivot the component 42 into the beam path is very small, i.e. considerably smaller than the path traveled by the component 42 on switching.

Starting from FIG. 4b), the component 42 is again pivoted out from the beam path, by means of the adjustment member 74 being moved clockwise back to the starting position shown in FIG. 4a). Starting from the starting position shown in FIG. 4a), the component 40 can now be pivoted into the beam path by moving the adjustment member 74 clockwise to the second operating position shown in FIG. 4c), which is the opposite to the first operating position, while the component 42 is held in the pivoted-out position, again by means of the magnetic interaction between the driven elements 70, 72 and the assigned driver elements 79, if appropriate assisted by the additional magnet 80. By moving the adjustment member 74 back from the second operating position shown in FIG. 4c) to the starting position shown in FIG. 4a), the component 40 is pivoted back out from the beam path.

The adjustment member 74 can be locked in the starting position, the first operating position and the second operating position. For this purpose, the operating lever 78 is equipped with a catch in the form of a ball 84 loaded by a spring 82i the housing 26 of the endoscope 10 being provided with three recesses 86 which are distributed about the circumference in accordance with the starting position, first operating position and second operating position of the adjustment member 74 and into which the ball 84 springs in each case.

It is clear from FIGS. 4a) to 4c) that the driver elements 76 and 79 in the form of the magnets are chosen, in respect of the polarity of the magnets, such that they form a complete force-lock with the corresponding driven elements 66, 68 and 70, 72, respectively, in the pivoted-in position of the component 40 and 42, respectively, while the driver elements 76 in the respectively pivoted-out state of the components 40 and 42 interact with the respective driven elements 66, 68 and 70, 72 in such a way that they exert on the respective support 48, 62 a torque towards the pivoted-out position, as a result of which the components 40 and 42 are held securely in their pivoted-out position.

What is claimed is:

1. A device for positioning at least one optical component inside an endoscopic system, comprising:
    a housing having an inside wall and a longitudinal axis, an optical axis of said endoscopic system extending through said housing and defining a light beam path,
    at least one carrier carrying said at least one component, said carrier being pivotable about a pivot axis extending substantially parallel to said longitudinal axis of said housing so that said at least one component can be pivoted into said light beam path and back out of said light beam path about said pivot axis,
    said pivot axis being arranged such that a smallest distance of said inside wall of said housing from said pivot axis is smaller than a greatest distance of said pivot axis to an outer edge of said at least one component,
    wherein a dimension of an interior of said housing from said longitudinal axis to said inside wall of said housing in a pivot plane of said at least one component is about 1½ to 2 times as great as a greatest dimension of said at least one component in said pivot plane.

2. The device of claim 1, wherein said distance of said outer edge of said at least one component from said pivot axis is preferably about two thirds of said dimension of said interior of said housing from said longitudinal axis to said inside wall of said housing.

3. The device of claim 1, wherein at least one further component is arranged in said housing, and wherein said at least one further component is assigned a further carrier separate from said carrier for said at least one optical component.

4. The device of claim 3, wherein said carrier and said at least one further carrier are arranged at axially about a same position relative to said longitudinal axis.

5. The device of claim 1, wherein at least one further component is arranged in said housing, and wherein said at least one further component is assigned a further carrier separate from said carrier for said at least one optical component, said at least one further carrier is pivotable about a further pivot axis which is offset by approximately 90° with respect to said pivot axis of said carrier for said at least one component in circumferential direction of said housing.

6. The device of claim 1, wherein at least one further component is arranged in said housing, and wherein said at least one further component is assigned a further carrier separate from said carrier for said at least one optical component, and wherein said at least one further carrier is arranged at an axially different position than said carrier for said at least one component relative to said longitudinal axis.

7. The device of claim 1, wherein, in order to pivot said at least one component, an actuating mechanism is provided which can be operated from outside said housing and which has at least one driver element cooperating with at least one driven element arranged on said carrier, wherein a distance of said at least one driver element from said pivot axis is small compared to a distance of a mid point of said at least one component from said pivot axis.

8. The device of claim 7, wherein said carrier is designed as a two-sided lever in relation to said pivot axis, said at least one driver element being arranged on that side of said pivot axis directed away from said at least one component.

9. The device of claim 1, wherein an actuating mechanism having an adjustment member is provided for said at least one optical component, wherein said adjustment member is adjustable in circumferential direction of said housing.

10. A device for positioning at least one optical component inside an endoscopic system, comprising:
a housing having an inside wall and a longitudinal axis, an optical axis of said endoscopic system extending through said housing and defining a light beam path,
at least one carrier carrying said at least one component, said carrier being pivotable about a pivot axis extending substantially parallel to said longitudinal axis of said housing so that said at least one component can be pivoted into said light beam path and back out of said light beam path about said pivot axis,
said pivot axis being arranged such that a smallest distance of said inside wall of said housing from said pivot axis is smaller than a greatest distance of said pivot axis to an outer edge of said at least one component,
wherein a distance of said outer edge of said at least one component from said pivot axis is in the range of between about a half to about three quarters of a dimension of an interior of said housing from the longitudinal axis to said inside wall of said housing.

11. The device of claim 10, wherein said distance of said outer edge of said at least one component from said pivot axis is preferably about two thirds of said dimension of said interior of said housing from said longitudinal axis to said inside wall of said housing.

12. The device of claim 10, wherein at least one further component is arranged in said housing, and wherein said at least one further component is assigned a further carrier separate from said carrier for said at least one optical component.

13. The device of claim 12, wherein said carrier and said at least one further carrier are arranged at axially about a same position relative to said longitudinal axis.

14. The device of claim 10, wherein at least one further component is arranged in said housing, and wherein said at least one further component is assigned a further carrier separate from said carrier for said at least one optical component, said at least one further carrier is pivotable about a further pivot axis which is offset by approximately 90° with respect to said pivot axis of said carrier for said at least one component in circumferential direction of said housing.

15. The device of claim 10, wherein at least one further component is arranged in said housing, and wherein said at least one further component is assigned a further carrier separate from said carrier for said at least one optical component, and wherein said at least one further carrier is arranged at an axially different position than said carrier for said at least one component relative to said longitudinal axis.

16. The device of claim 10, wherein, in order to pivot said at least one component, an actuating mechanism is provided which can be operated from outside said housing and which has at least one driver element cooperating with at least one driven element arranged on said carrier, wherein a distance of said at least one driver element from said pivot axis is small compared to a distance of a mid point of said at least one component from said pivot axis.

17. The device of claim 16, wherein said carrier is designed as a two-sided lever in relation to said pivot axis, said at least one driver element being arranged on that side of said pivot axis directed away from said at least one component.

18. The device of claim 10, wherein an actuating mechanism having an adjustment member is provided for said at least one optical component, wherein said adjustment member is adjustable in circumferential direction of said housing.

19. A device for positioning at least one optical component inside an endoscopic system, comprising:
a housing having an inside wall and a longitudinal axis, an optical axis of said endoscopic system extending through said housing and defining a light beam path,
at least one carrier carrying said at least one component, said carrier being pivotable about a pivot axis extending substantially parallel to said longitudinal axis of said housing so that said at least one component can be pivoted into said light beam path and back out of said light beam path about said pivot axis,
said pivot axis being arranged such that a smallest distance of said inside wall of said housing from said pivot axis is smaller than a greatest distance of said pivot axis to an outer edge of said at least one component,
wherein at least one further component is arranged in said housing, and wherein said at least one further component is assigned a further carrier separate from said carrier for said at least one optical component, and wherein an actuating mechanism having an adjustment member is provided in such a way that, when said adjustment member is moved from a starting position, in which both components are pivoted out from said light beam path, to a first operating position, one of said at least one component and said at least one further component is pivoted into said light beam path, and, when said adjustment member is moved from said starting position to a second operating position opposite to said first operating position, the other of said at least one component and said at least one further component is pivoted into said light beam path.

20. The device of claim 19, wherein, in said first and second operating positions, the one of said components respectively pivoted-out is held securely in the pivoted-out position.

21. The device of claim 20, wherein said adjustment member can be locked in said starting position and at least one of said first and second operating positions.

22. A device for positioning at least one optical component inside an endoscopic system, comprising:
- a housing having an inside wall and a longitudinal axis, an optical axis of said endoscopic system extending through said housing and defining a light beam path,
- at least one carrier carrying said at least one component, said carrier being pivotable about a pivot axis extending substantially parallel to said longitudinal axis of said housing so that said at least one component can be pivoted into said light beam path and back out of said light beam path about said pivot axis,
- said pivot axis being arranged such that a smallest distance of said inside wall of said housing from said pivot axis is smaller than a greatest distance of said pivot axis to an outer edge of said at least one component,
- wherein an actuating mechanism is provided for said at least one optical component, said actuating mechanism having at least one driver element and at least one driven element, said at least one driver element and said at least one driven element are designed as magnetically acting elements and interact magnetically through said housing.

* * * * *